(12) United States Patent
Miyako et al.

(10) Patent No.: US 7,839,968 B2
(45) Date of Patent: Nov. 23, 2010

(54) RADIATION IMAGE CAPTURING APPARATUS

(75) Inventors: Kuniaki Miyako, Minami-ashigara (JP);
Hajime Nakata, Minami-ashigara (JP);
Kazuo Hakamata, Odawara (JP);
Yasunori Ohta, Yokohama (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/212,860

(22) Filed: Sep. 18, 2008

(65) Prior Publication Data

US 2009/0080605 A1 Mar. 26, 2009

(30) Foreign Application Priority Data

Sep. 21, 2007 (JP) ............................. 2007-245092

(51) Int. Cl.
*A61B 6/04* (2006.01)
(52) U.S. Cl. ...................................... 378/37; 378/189
(58) Field of Classification Search .................. 378/37, 378/189, 190, 199
See application file for complete search history.

(56) References Cited

U.S. PATENT DOCUMENTS

| 6,268,614 B1 | 7/2001 | Imai | |
| 7,085,346 B1 * | 8/2006 | Virta et al. | 378/37 |
| 2006/0126782 A1 * | 6/2006 | Pohan et al. | 378/19 |

FOREIGN PATENT DOCUMENTS

JP 2000-37374 A 2/2000

* cited by examiner

*Primary Examiner*—Hoon Song
(74) *Attorney, Agent, or Firm*—Sughrue Mion, PLLC (57) ABSTRACT

An image capturing base that contains a radiation detector includes a housing having a slit serving as an air inlet port formed in the front end side of the housing, which is to be located adjacent to the chest wall of a subject, and a slit serving as an air outlet port formed in the rear end side of the housing adjacent to a pivot shaft. A fan forces air to flow into the housing through the slit, along a detection surface of the radiation detector in a direction from the front end side toward the rear end side, and out of the housing through the slit.

6 Claims, 7 Drawing Sheets

RADIATION IMAGE CAPTURING APPARATUS

BACKGROUND OF THE INVENTION

1. Field of the Invention

The present invention relates to a radiation image capturing apparatus that includes a radiation detector for detecting a radiation image of a subject and generating electrical signals representing the detected radiation image. More particularly, the present invention concerns a radiation image capturing apparatus that includes a mechanism for cooling the radiation detector.

2. Description of the Related Art

In a radiation image capturing apparatus, such as an X-ray breast image capturing apparatus (e.g., a mammography apparatus) or the like, a radiation image is generated by exposing a subject (patient) to radiation and recording the radiation in a radiation image recording unit (i.e., a radiation detector). The radiation image recording unit is thereafter scanned with reading light emitted from a reading light source, which is moved relative to the radiation image recording unit, in order to read out therefrom the information associated with the recorded radiation image. An example of such a radiation image capturing apparatus is disclosed in U.S. Pat. No. 6,268,614, which is incorporated herein by reference in its entirety.

Examples of a radiation image recording unit, which can be used in the above-mentioned apparatus, include a radiation detector having a plurality of photoelectric conversion elements and thin-film transistors (TFT), or a light readout type, a light conversion type, or a direct conversion type of radiation detector.

In such a radiation image capturing apparatus, it is necessary to maintain a proper temperature range because of constraints on the temperature characteristics of the photoelectric conversion elements, the effects of thermal noise generated by the electrical circuit, and the like. Therefore, a radiation image capturing apparatus is provided with an air or water type of cooler therein. One example of such an apparatus is disclosed in Japanese Laid-Open Patent Publication No. 2000-037374, which is incorporated herein by reference in its entirety.

The radiation image capturing apparatus disclosed in Japanese Laid-Open Patent Publication No. 2000-037374 is directed to effective cooling of the radiation detector. As can be seen in FIG. 1 of the above-mentioned publication, the radiation image capturing apparatus includes a two-dimensional radiation detector 5 and a signal converter 6, which are contained in the housing 4 of an image capturing unit 3 in this order from the front of the housing 4. The housing 4 is provided with a fan 7, which acts as a cooling means, on an upper portion thereof. A lower portion of the housing 4 is provided with an inlet port 4a for introducing outside air. Release of heat generated by the two-dimensional radiation detector 5 is accomplished by actuating the fan 7, and thereby introducing air into the housing 4 through the inlet port 4a.

In the apparatus disclosed in Japanese Laid-Open Patent Publication No. 2000-037374, the inlet port 4a is formed at one end of the radiation detector 5, while the fan 7 is located at the other end of the radiation detector 5 so that cooling of the whole radiation detector 5 can be achieved. In many radiation image capturing apparatuses, however, the arrangement of the radiation detector within the image capturing unit is restricted for various reasons. If the image capturing unit is a mammography apparatus, for example, the image capturing unit is required to be movable around the breast, so that image capturing of the breast from different directions can be performed. Consequently, a large size for the image capturing unit housing is not permitted, and the radiation detector must be contained within a small space. Furthermore, since image capturing up to the base of the breast is required, the radiation detector must be located within the housing such that the distance between the radiation detector and the chest wall of the patient becomes suitably short during a mammography examination. Thus, the radiation detector is located on the chest-wall side of the housing, forming a narrow space between the radiation detector and the portion of the housing nearest to the chest wall of the subject. Such an arrangement causes insufficient heat to be released from the radiation detector. This results in non-uniform cooling of the radiation detector, which in turn tends to reduce imaging accuracy.

SUMMARY OF THE INVENTION

It is an object of the invention to provide a radiation image capturing apparatus that allows uniform cooling of a radiation detector even when constraints exist on the arrangement of the radiation detector.

A radiation image capturing apparatus according to the invention comprises a radiation detector for detecting a radiation image using a detection surface and generating electrical signals corresponding to the radiation image, and a housing containing the radiation detector. The housing includes a front end side, a rear end side, an inlet port for a cooling medium formed in the front end side, and an outlet port for the cooling medium formed in the rear end side. The cooling medium is introduced into the housing through the inlet port, flows through the housing from the front end side toward the rear end side along the detection surface of the radiation detector, and is discharged through the outlet port.

According to the invention, the cooling medium flowing along the detection surface of the radiation detector from the front end side toward the rear end side of the housing cools the front end of the radiation detector and portions thereof in proximity to the front end. Thus, even if the radiation detector is arranged within the housing such that heat tends to accumulate at the front end side of the housing, the accumulated heat can be released efficiently, and thus uniform cooling of the entire detection surface of the radiation detector can be achieved.

The radiation image capturing apparatus preferably includes a fan that forces the cooling medium to flow from the inlet port to the outlet port. This configuration ensures that the cooling medium flows within the housing.

The inlet port is preferably formed on both left and right sides of the housing and/or on an underside of the housing. In a mammography apparatus, for example, since the front surface of the housing faces toward the subject, whereas the subject's breast is placed on the upper surface, both surfaces are inadequate for introduction of the cooling medium. Therefore, in the present invention, the cooling medium is introduced into the housing from right and left sides and from the underside of the housing, thereby allowing the cooling medium to be introduced reliably into the housing.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
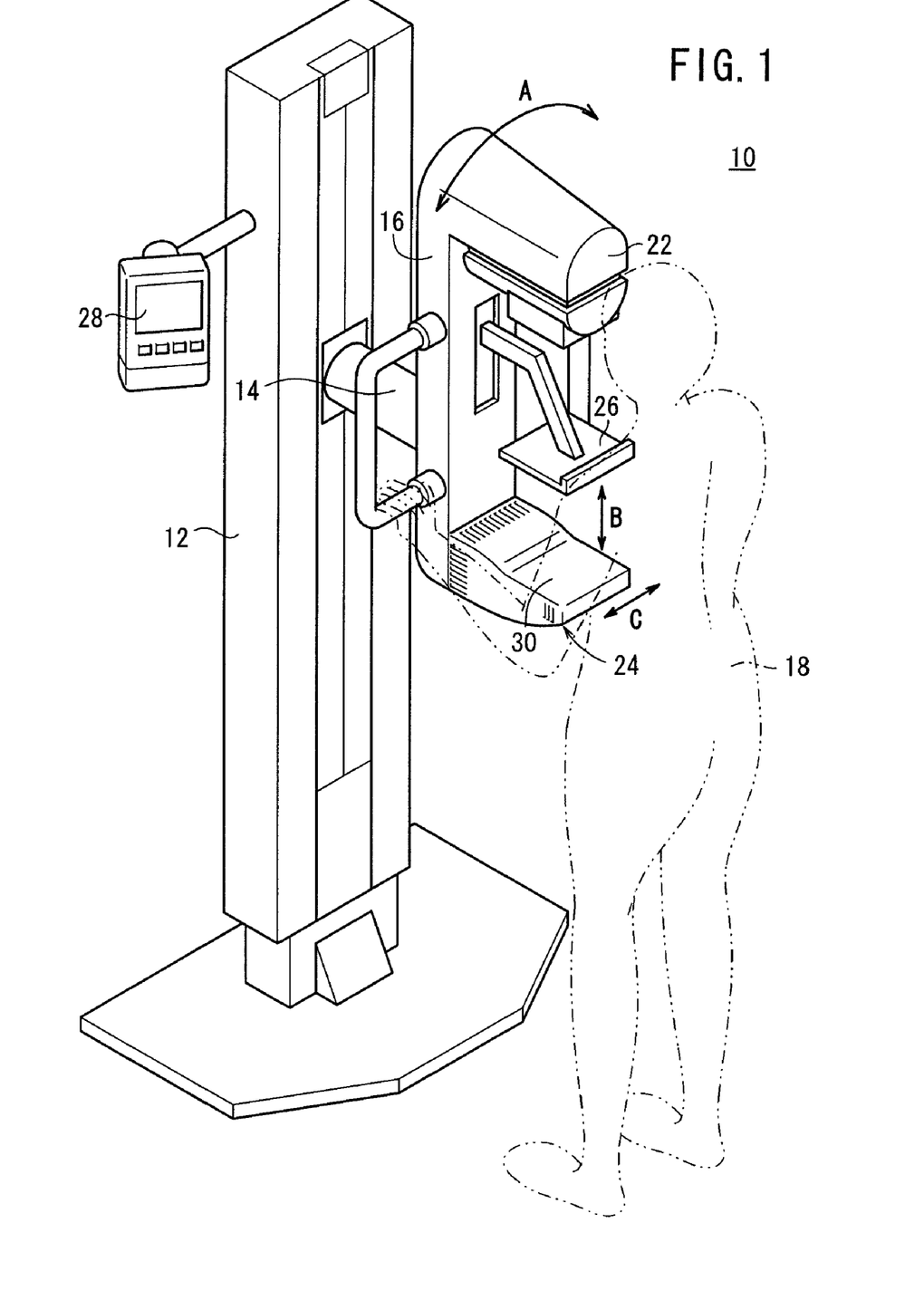
FIG. 1 is a perspective view of a mammography apparatus constituting a radiation image capturing apparatus according to an embodiment of the present invention.

FIG. 1 shows a perspective view of an embodiment of a radiation image capturing apparatus according to the present invention, which is a mammography apparatus 10 for breast cancer screening or the like.

The mammography apparatus 10 includes an upstanding base 12, an arm 16 fixed to a pivot shaft 14 that is connected substantially centrally to the base 12, a radiation source housing unit 22 fixed to one end of the arm 16 and housing a radiation source (not shown) therein for applying radiation X or other recordable electromagnetic waves to a breast 20 (see FIG. 2), which constitutes a site of the subject 18 to be imaged, an image capturing base 24 fixed to the other end of the arm 16 in opposition to the radiation source housing unit 22, and a compression plate 26 for holding the breast 20 by compressing the breast 20 against the image capturing base 24.

The arm 16 holding the radiation source housing unit 22 and the image capturing base 24 can be rotated about the pivot shaft 14 in the directions indicated by the double-headed arrow A, so as to adjust the image capturing direction of the breast 20 of the subject 18. The compression plate 26 is connected to the arm 16 between the radiation source housing unit 22 and the image capturing base 24, so as to be movable in the directions shown by the double-headed arrow B.

The base 12 also is provided with a display-control unit 28 for displaying image capturing information of the image obtained by the mammography apparatus 10, together with identification (ID) information or the like of the subject 18. The image capturing information includes the image capturing site, an image capturing direction, or the like, of the image of the subject 18 produced with the mammography apparatus 10. The display-control unit 28 also allows settings for the aforementioned information to be made, if desired.

Figure 2:
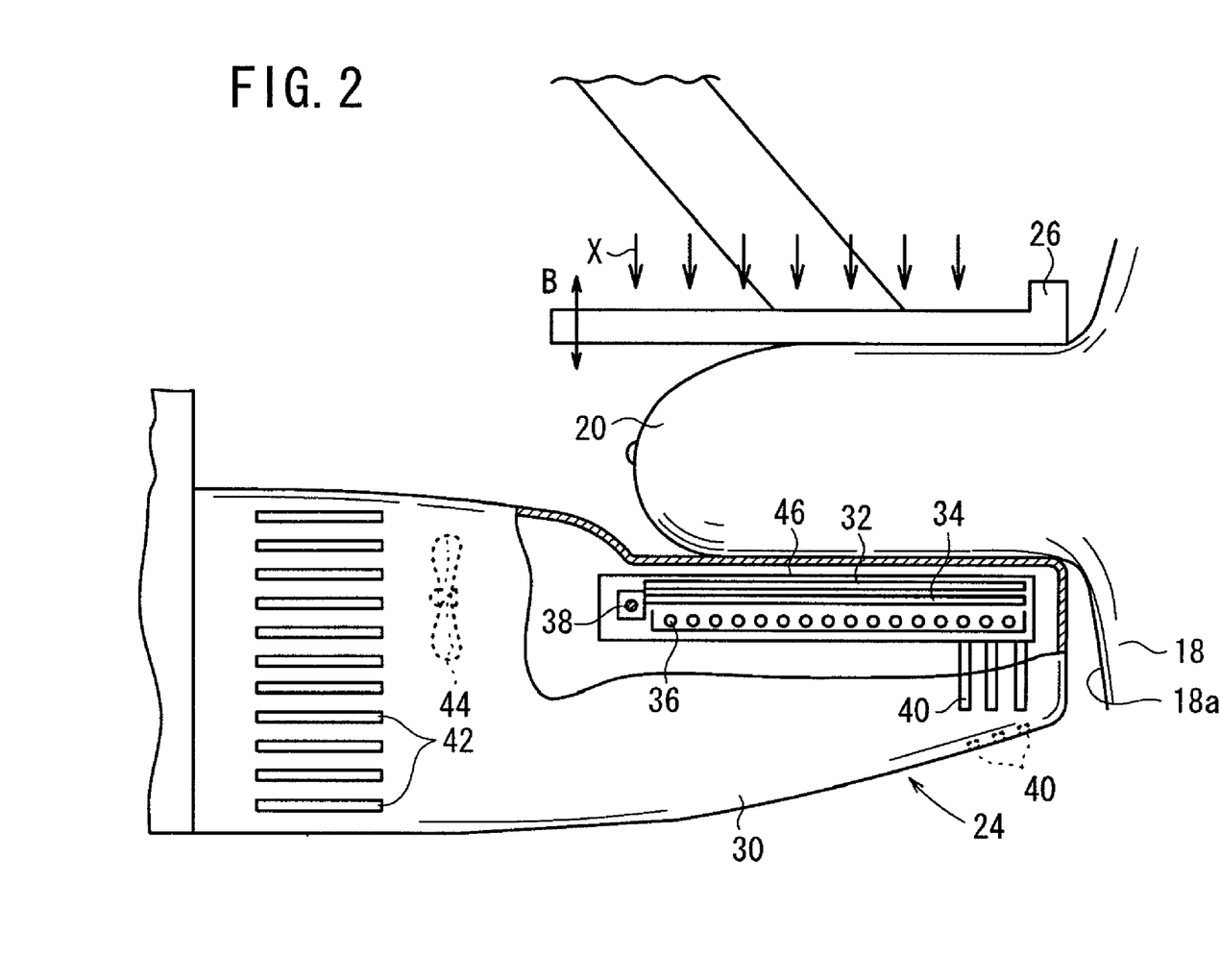
FIG. 2 is a partial cross-sectional side view of a portion of the mammography apparatus of FIG. 1, including the image capturing base, and further showing the internal structure thereof.

FIG. 2 is a partial cross-sectional view of a portion of the mammography apparatus 10, showing the internal structure of the image capturing base 24. FIG. 2 shows the site of the subject 18 to be imaged, which is the breast 20, being placed between the image capturing base 24 and the compression plate 26.

A planar radiation detector 32 is contained within the housing 30 of the image capturing base 24. The radiation detector 32 stores radiation image information, which is captured in the radiation source housing unit 22 based on the radiation X emitted from the radiation source, and converts the radiation image information into electric signals. Also contained within the housing 30 is a reading light source 34 that applies linear reading light onto the radiation detector 32 in order to read out the radiation image information recorded therein. Further disposed within the housing 30 is an erasing light source 36, which applies erasing light onto the radiation detector 32. The reading light source 34 may be moved with a scanning mechanism 38 in a direction perpendicular to the plane of FIG. 2 (the direction indicated by the arrow C in FIG. 1) so that the reading light scans over the radiation detector 32.

As shown in FIG. 2, the chest-wall side (front end side) of the housing 30, i.e., the side of the housing 30 that is located adjacent to the chest wall 18a of the subject 18, is provided on under and side surfaces of the housing 30, with a plurality of slits 40 that serve as inlet ports for introducing outside air into the housing 30. Further, the pivot-shaft side (rear end side) of the housing 30, i.e., the side of the housing 30 adjacent to the pivot shaft 14, is provided with a plurality of slits 42, which are arranged around the periphery of the housing 30, serving as outlet ports for discharging the air that is introduced through the slits 40. Furthermore, two fans 44 are provided inside the housing 30 between the slits 40 and the slits 42, in order to deliver air introduced through the slits 40 toward the slits 42 (see FIG. 3B).

The radiation detector 32 is a direct-conversion, light-reading solid-state detector. The radiation detector 32 stores radiation image information, which is produced based on the radiation X that has passed through the breast 20, as an electrostatic latent image. Further, when scanned by the reading light from the reading light source 34, the radiation detector 32 generates an electric current corresponding to the amount of electric charge of the electrostatic latent image. An example of a radiation detector that may be utilized in the present embodiment is disclosed in U.S. Pat. No. 6,268,614.

Operations of the mammography apparatus 10 according to the present embodiment, which is configured as indicated above, shall now be described.

First, ID information of the subject 18, image capturing conditions, or the like is supplied to the mammography apparatus 10 through a console (not shown), an ID card, or the like. The ID information may include the name, age, sex, etc., of the subject 18 and can be acquired from an ID card of the subject 18. If the mammography apparatus 10 is connected to a network, the ID information may also be acquired from other devices on the network. The image capturing conditions may include the image capturing site, the image capturing direction, and the like, as specified by the physician. These items of information may be acquired from a higher-level apparatus on the network, or entered through the console by a radiologist. The ID information, image capturing conditions, or the like may be displayed on the display-control unit 28 of the mammography apparatus 10 for verification.

The radiologist then sets up the mammography apparatus 10 according to specified image capturing conditions. The image capturing direction of the breast 20 may include, for example, a cranio-caudal view (CC), a medio-lateral view (ML), and a medio-lateral oblique view (MLO), in which an image is captured by exposing the breast 20 to x-rays from the top, side, and from an oblique angle, respectively. The arm 16 is rotated about the pivot shaft 14 in accordance with the specified image capturing direction.

Next, the breast 20 of the subject 18 is positioned with respect to the mammography apparatus 10, i.e., the breast 20 is placed on the image capturing base 24 and the compressing plate 26 is moved down to hold the breast 20 in position between the image capturing base 24 and the compressing plate 26 (see FIG. 2).

After the above preparatory operation has been completed, the radiation source (not shown) in the radiation source housing unit 22 is activated in order to expose the breast 20 to radiation X, in accordance with predetermined image capturing conditions. The radiation X that has passed through the breast 20 negatively charges the radiation detector 32 so as to form a latent image thereon. Negative charging of the radiation detector 32 may be achieved in accordance with the method disclosed in U.S. Pat. No. 6,268,614, for example.

After the latent image has been recorded in the radiation detector 32, the reading light source 34 (see FIG. 2) is moved by the scanning mechanism 38 in the direction indicated by the arrow C of FIG. 1 (auxiliary direction) to scan the reading light that is emitted from the reading light source 34 over the radiation detector 32. A processing circuit (not shown) reads out the radiation image information from the radiation detector 32. Further details concerning readout processing may be understood from the above-mentioned U.S. Pat. No. 6,268,614, which discloses the applicable processing.

During recording of the radiation image information on the radiation detector 32 as well as during readout therefrom, heat is generated from the radiation detector 32 as well as from other devices that are arranged within the housing 30 of the image capturing base 24. This causes heat to be accumulated and thus the temperature increases inside the housing 30, which may result in abnormal operation of the radiation detector 32. As already mentioned, the space formed between the radiation detector 32 and the portion of the housing 30 nearest to the chest wall 18a of the subject 18 is quite narrow, thus making it difficult to release the heat generated by the radiation detector 32. In the present embodiment, however, cooling of the inner space of the housing 30, and in particular, cooling of the narrow space mentioned above can be achieved in the following manner.

Figure 3A:
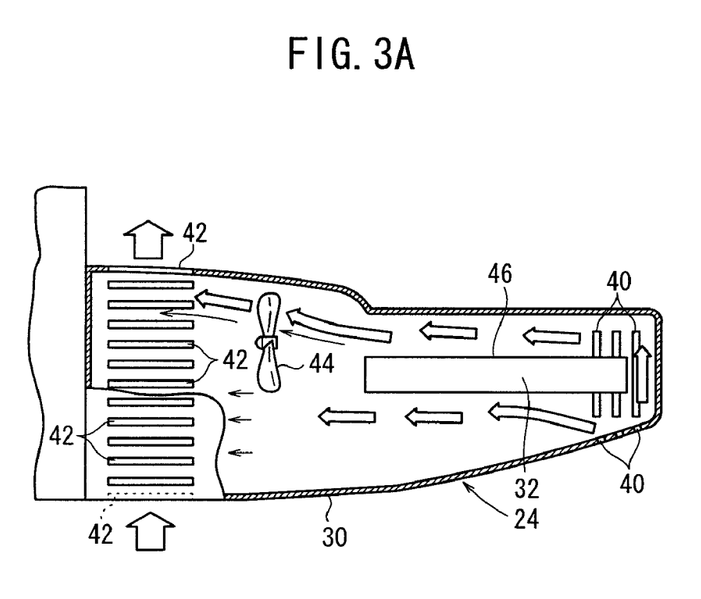
FIG. 3A is a cross-sectional side view of the image capturing base of FIG. 2, showing the airflow therein.
Figure 3B:
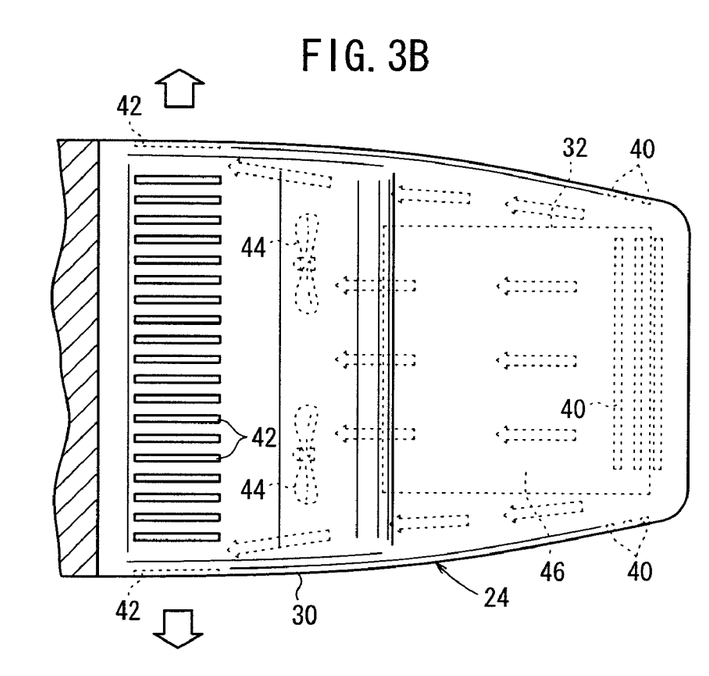
FIG. 3B is a plan view of the image capturing base of FIG. 2, showing the airflow therein.
Figure 4:
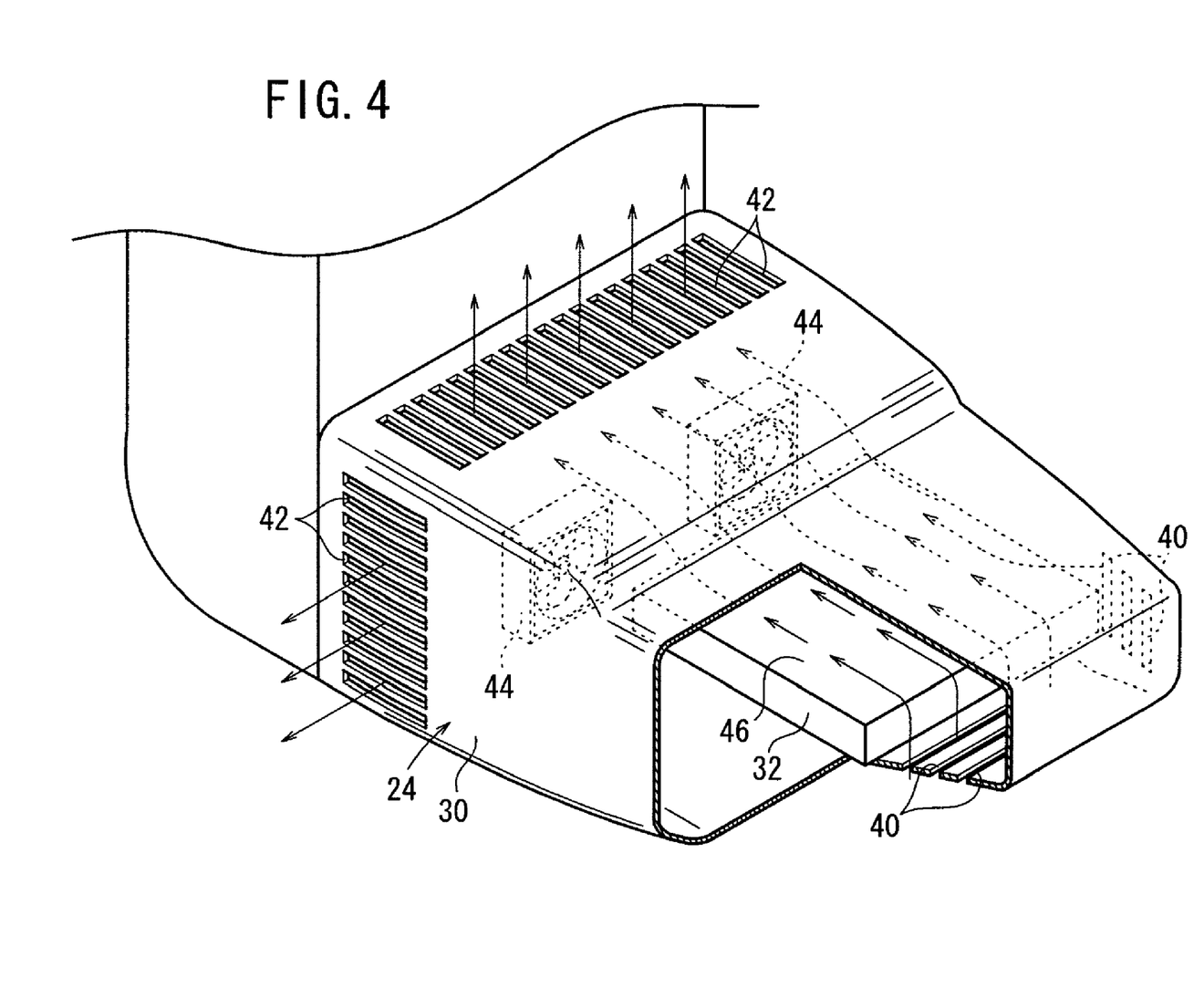
FIG. 4 is a partial cutaway perspective view of the image capturing base of FIG. 2, showing the airflow therein.

FIGS. 3A, 3B, and 4 show, respectively, a cross-sectional side view, a plan view, and a partial cutaway perspective view of the image capturing base 24, illustrating the airflow inside the image capturing base 24.

As shown in FIGS. 3A, 3B, and 4, when the fan 44 is actuated, relatively high temperature air (i.e., air having a temperature higher than that of the outside air) around the radiation detector 32 is forced to flow toward the pivot-shaft side of the housing 30 along the detection surface 46 of the radiation detector 32. Such air is then released from the image capturing base 24 and through the slits 42 in the pivot-shaft side of the housing 30. As the relatively high temperature air flows toward the pivot shaft 14, outside air flows into the housing 30 through the slits 40 in the chest-wall side of the housing 30.

In FIGS. 3A and 3B, the radiation detector 32 is shown as a simple block diagram, while the other components, such as the reading light source 34 and the erasing light source 36, have been omitted for purposes of simplicity. FIGS. 4, 5A, 5B, 6A, 6B, 7A and 7B have been simplified in the same manner.

As described above, the housing 30 of the image capturing base 24 according to the present embodiment includes slits 40 and slits 42, which are formed, respectively, in the chest-wall side of the housing 30 to serve as air inlet ports, and in the pivot-shaft side of the housing 30 to serve as air outlet ports. Thus, outside air is introduced into the housing 30 through the slits 40, the air flows along the detection surface 46 of the radiation detector 32 from the chest-wall side toward the pivot-shaft side of the housing 30, and finally flows out of the housing 30 through the slits 42.

Since, according to the present embodiment, air is allowed to flow along the detection surface 46 of the radiation detector 32 from the chest-wall side toward the pivot-shaft side of the housing 30, effective cooling of the radiation detector 32 at and around the end thereof nearest to the chest wall 18a of the subject 18 can be achieved. In other words, even though the radiation detector 32 is arranged such that heat tends to accumulate at the end nearest to the chest wall 18a of the subject 18, the accumulated heat can be released efficiently, and thus uniform cooling of the entire detection surface 46 of the radiation detector 32 can be achieved.

The slits 40 are formed in both of the left and right sides as well as on the underside of the housing 30. In the mammography apparatus 10, for example, the front and upper surfaces of the housing 30 come into contact with the chest wall 18a and the breast 20, respectively, thereby making it difficult to introduce air therethrough. The present embodiment ensures that air may be introduced into the housing 30 by allowing the air to flow through the left, the right and the underside of the housing.

The present invention is not limited to the aforementioned embodiment. Various changes and modifications may be made in light of the descriptions provided herein without departing from the spirit and scope of the invention as set forth in the appended claims.

The radiation image capturing apparatus is not limited to a mammography apparatus 10, as discussed in the aforementioned embodiment, but may also be another type of radiation image capturing apparatus, such as those utilizing electronic cassettes, for example.

Instead of a direct-conversion type radiation detector, as used in the embodiment mentioned above, a radiation detector may be employed that comprises a scintillator for converting radiation X into visible light, with a photoconductive recording layer that generates electrical charge pairs when exposed to such visible light. Further, another type of radiation detector may be utilized, which includes a photoelectric conversion layer for converting an amount of radiation X applied thereto directly into electrical signals.

Figure 5A:
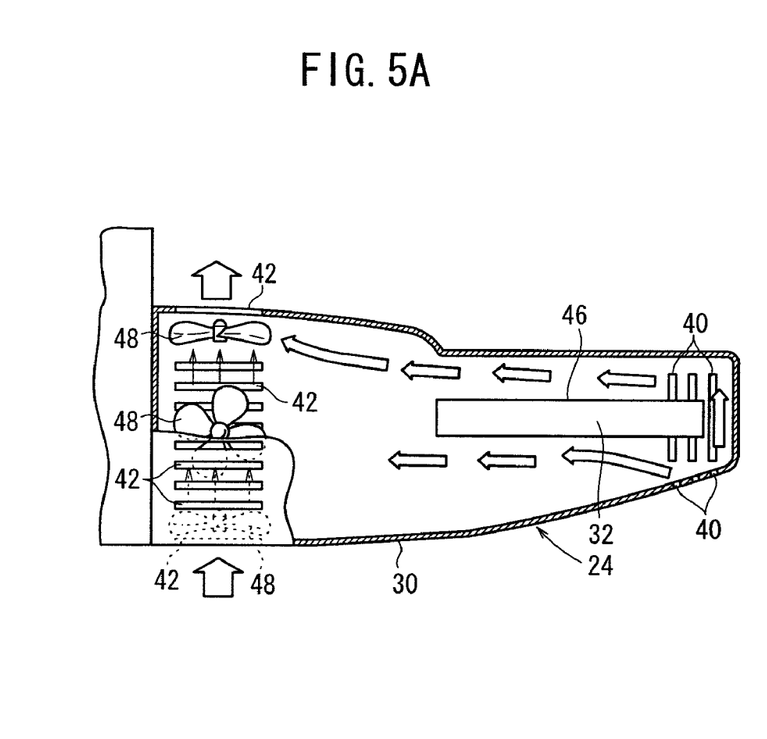
FIG. 5A is a cross-sectional side view of a first modification of the image capturing base, showing the airflow therein.
Figure 5B:
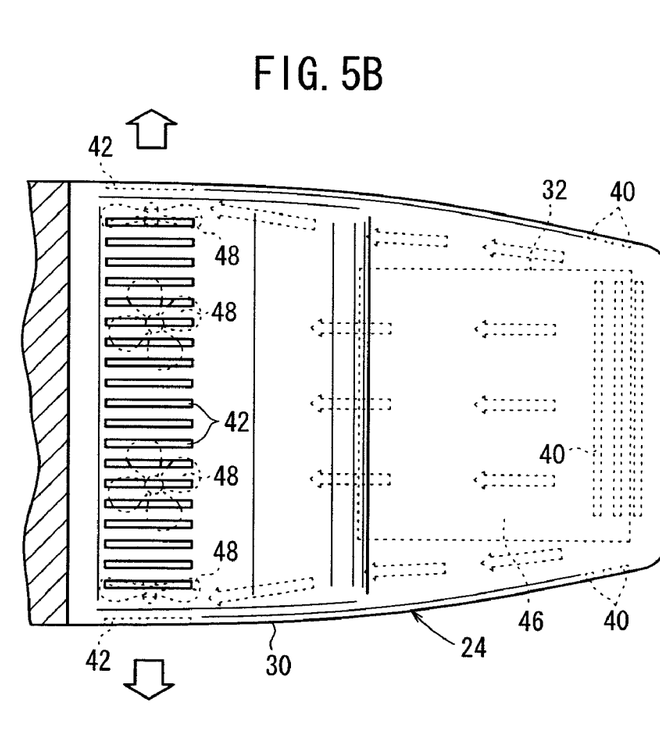
FIG. 5B is a plan view of the first modification of the image capturing base, showing the airflow therein.

Although the above-mentioned embodiment achieves cooling of the radiation detector 32 by means of airflow in the housing 30 generated by the fan 44 disposed between the slits 40 and 42, cooling of the radiation detector 32 may be performed in various ways. For example, as shown in FIGS. 5A and 5B, a plurality of fans 48 may be provided on the pivot-shaft side of the housing 30, two of the fans 48 being disposed on the top and bottom walls and one on each sidewall of the housing 30, so that air is forced to flow from an underside toward an upper side of the housing 30 in order to achieve cooling of the radiation detector 32. A sensor (not shown) for detecting an angular orientation of the housing 30 with respect to the base 12 may be provided in the housing 30, or on the pivot shaft 14, etc., so as to determine which one of the fans 48 should be actuated as an inlet or outlet fan. For example, based on the output of the sensor, the fan 48 that is determined to be on the underside of the housing 30 may be actuated as an inlet fan, whereas the fan 48 on the upper side may be actuated as an outlet fan. It should be noted that the number of fans 48 according to the exemplary configuration shown in FIGS. 5A and 5B is not limited to six, and the housing 30 may be provided with any number of one or more fans. Further, the arrangement of fans 48 is not restricted to the configuration shown in FIGS. 5A and 5B, and such an arrangement can be modified, if desired.

Figure 6A:
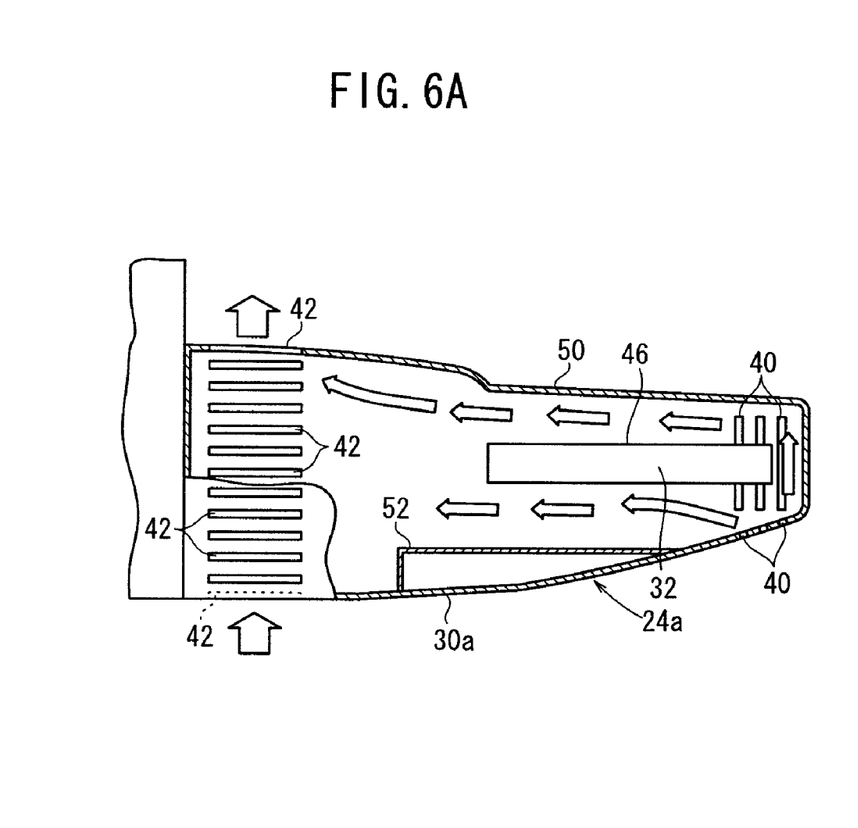
FIG. 6A is a cross-sectional side view of a second modification of the image capturing base, showing the airflow therein.
Figure 6B:
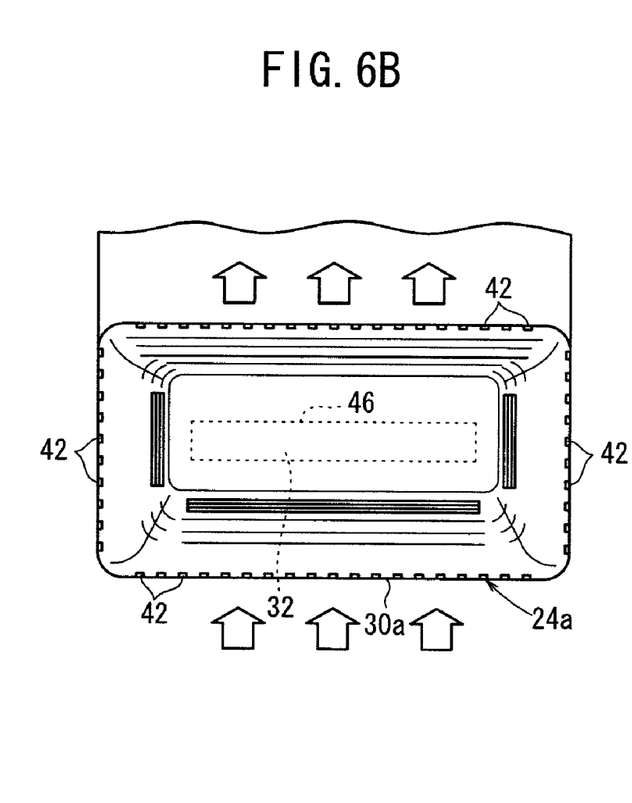
FIG. 6B is a front view of the second modification of the image capturing base, showing the airflow therein.

It should further be noted that an image capturing base 24a, which does not have any fans, may also be utilized as shown in FIGS. 6A and 6B. Instead of employing a fan, the image capturing base 24a is provided with a housing 30a having a wall 50 that is inclined upwardly from the chest-wall side toward the pivot-shaft side of the housing 30a. The inclination of the wall 50 allows relatively high temperature air around the detection surface 46 of the radiation detector 32 to move up along the wall 50 and out of the housing 30a through the slits 42. Movement of such relatively high temperature air causes outside air, which flows into the housing 30a through the slits 40, to cool the radiation detector 32.

The housing 30a may also be provided with a second wall 52, which is formed below the radiation detector 32 as shown in FIG. 6A (i.e., on a side of the housing 30a opposite to the detection surface 46), so that air introduced through the slits 40 can flow smoothly inside the housing 30.

Figure 7A:
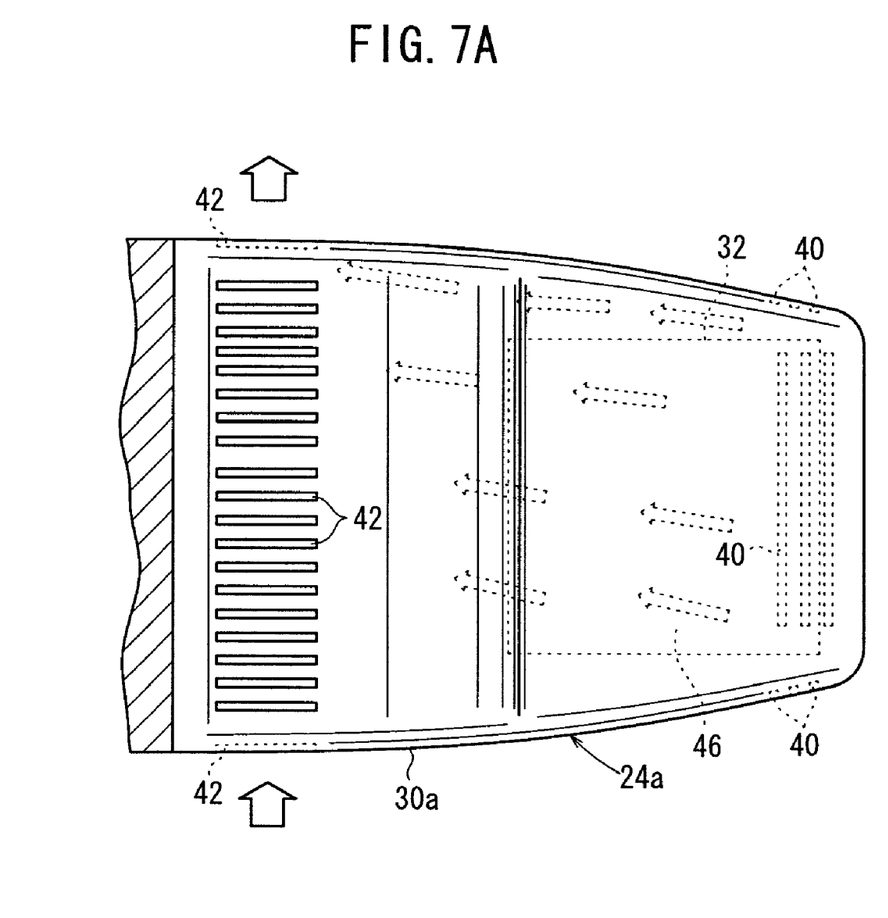
FIG. 7A is a side view of the image capturing base of FIG. 6A, in which the image capturing base is pivoted 90 degrees around a pivot shaft from the position shown in FIG. 6A, and showing the airflow within the image capturing base.
Figure 7B:
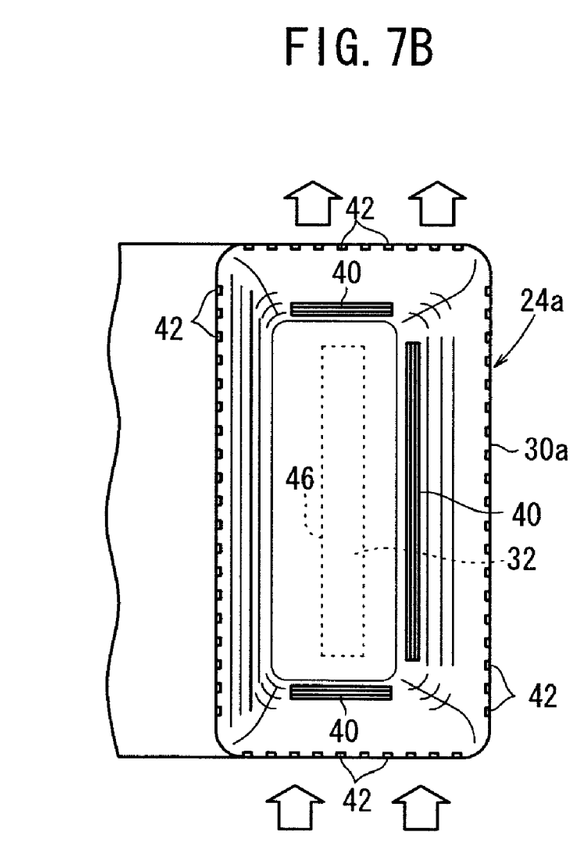
FIG. 7B is a front view of the image capturing base of FIG. 6B, wherein the image capturing base is pivoted 90 degrees around a pivot shaft from the position in FIG. 6B, and showing the airflow within the image capturing base.

FIGS. 7A and 7B show the image capturing base 24a of FIGS. 6A and 6B pivoted 90 degrees from the position shown in FIG. 6A. The walls of the housing 30a are formed so as to incline upwardly toward the slits 42 and facilitate discharge of the relatively high temperature air even when the image capturing base 24a is oriented as shown in FIGS. 7A and 7B.

It should be understood that the plurality of slits 40 provided on the chest-wall side of the housing 30 may be replaced with louvers or other openings that allow outside air to flow into the housing 30. Likewise, the plurality of slits 42 provided on the pivot-shaft side of the housing 30 may be replaced with louvers or other openings that allow air to be discharged from the housing 30. Further, the number of slits 40, 42 provided in the housing 30 may be altered, if desired.

What is claimed is:

1. A mammography apparatus, comprising:
    a base;
    a compression plate for compressing a breast;
    a radiation detector for detecting a radiation image of a subject using a detection surface and generating electrical signals corresponding to the radiation image; and
    a housing containing said radiation detector, said housing including a front end side, which is opposite to said base, a rear end side, which is closer to said base than the front end side is to said base, an inlet port for a cooling medium formed in said front end side, and an outlet port for the cooling medium formed in said rear end side,
    wherein the cooling medium is introduced into said housing through said inlet port, flows through said housing from said front end side toward said rear end side along said detection surface of said radiation detector extending from said front end side to said rear end side, and is discharged through said outlet port.

2. The mammography apparatus according to claim 1, further comprising:
    a fan that forces the cooling medium to flow from said inlet port to said outlet port.

3. The mammography apparatus according to claim 1, wherein said inlet port is formed on both left and right sides of said housing.

4. The mammography apparatus according to claim 1, wherein said inlet port is formed on an underside of said housing.

5. The mammography apparatus according to claim 1, wherein the housing is configured such that the subject which is a patient's breast is positioned above an upper surface of the housing and the front end side of the housing faces a chest wall of the patient, when the patient stands facing the front end side of the housing to be positioned for mammography.

6. A mammography apparatus, comprising:
    a base;
    a compression plate;
    a radiation detector for detecting a radiation image of a subject positioned between the compression plate and the radiation detector using a detection surface and generating electrical signals corresponding to the radiation image; and
    a housing containing said radiation detector, said housing including a front end side, which is opposite to said base, a rear end side, which is closer to said base than the front end side is to said base, an inlet port for a cooling medium formed in said front end side, and an outlet port for the cooling medium formed in said rear end side,
    wherein the cooling medium is introduced into said housing through said inlet port, flows through said housing from said front end side toward said rear end side along said detection surface of said radiation detector extending from said front end side to said rear end side, and is discharged through said outlet port.

* * * * *